(12) United States Patent
Grant

(10) Patent No.: US 7,909,880 B1
(45) Date of Patent: Mar. 22, 2011

(54) TOE CAP IMPLANT

(76) Inventor: William P. Grant, Virginia Beach, VA (US)

( * ) Notice: Subject to any disclaimer, the term of this patent is extended or adjusted under 35 U.S.C. 154(b) by 200 days.

(21) Appl. No.: 12/156,667

(22) Filed: Jun. 3, 2008

Related U.S. Application Data

(60) Provisional application No. 60/933,021, filed on Jun. 4, 2007.

(51) Int. Cl.
*A61F 2/42* (2006.01)
(52) U.S. Cl. ..................................... 623/21.19
(58) Field of Classification Search ............... 623/11.11, 623/16.11, 18.11, 21.11–21.19, 23.42
See application file for complete search history.

(56) References Cited

U.S. PATENT DOCUMENTS

| | | | | |
|---|---|---|---|---|
| 5,037,440 | A | * | 8/1991 | Koenig ...................... 623/21.19 |
| 5,108,443 | A | * | 4/1992 | Branemark ................. 623/21.15 |
| 6,520,964 | B2 | * | 2/2003 | Tallarida et al. ................ 606/71 |
| 2006/0074492 | A1 | * | 4/2006 | Frey ........................... 623/21.15 |

FOREIGN PATENT DOCUMENTS

FR 2709663 A1 * 3/1995

OTHER PUBLICATIONS

Translation of FR2709663A1.*

* cited by examiner

*Primary Examiner* — Corrine M McDermott
*Assistant Examiner* — Megan Wolf
(74) *Attorney, Agent, or Firm* — Christopher John Rudy

(57) ABSTRACT

Toe cap implant for correction of Hallux Rigidus has a cap having a head with a convex articular surface and opposite the articular surface an attaching feature that can attach the cap to a bone screw. The cap and screw can provide for an ensemble or a kit.

12 Claims, 2 Drawing Sheets

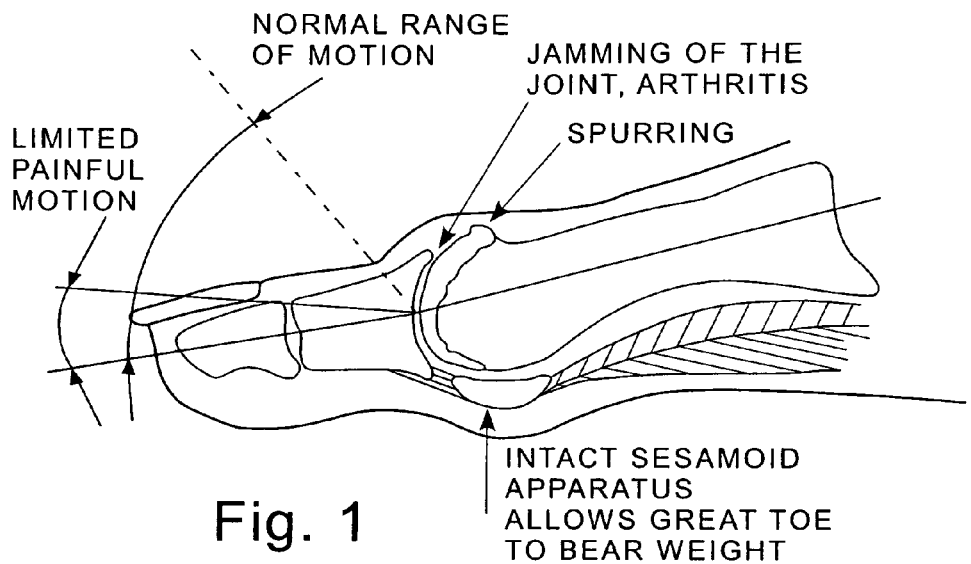
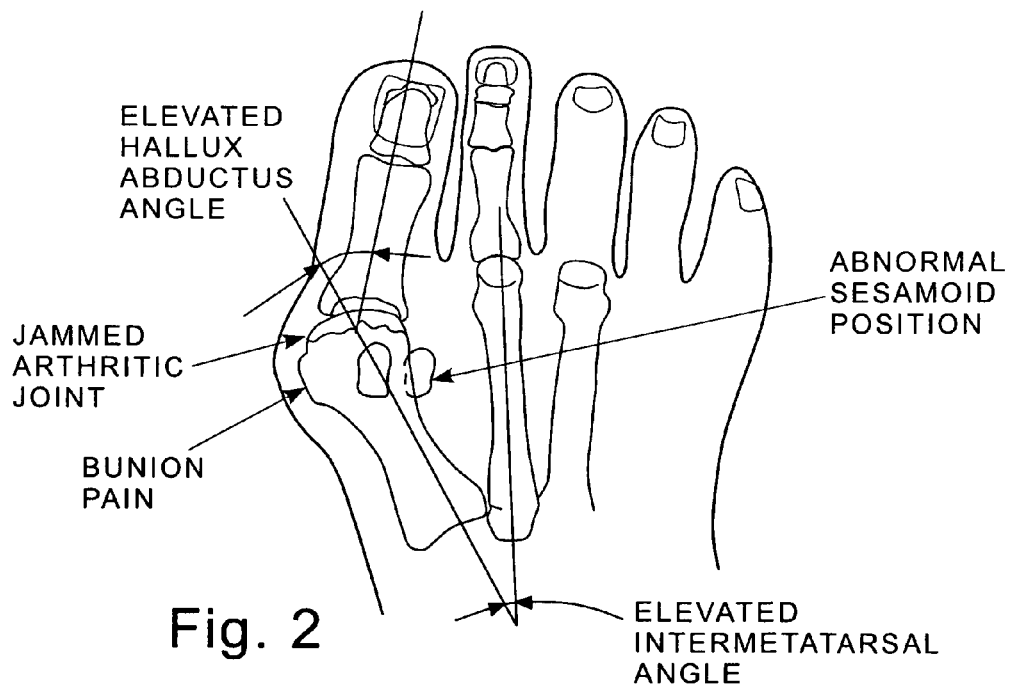

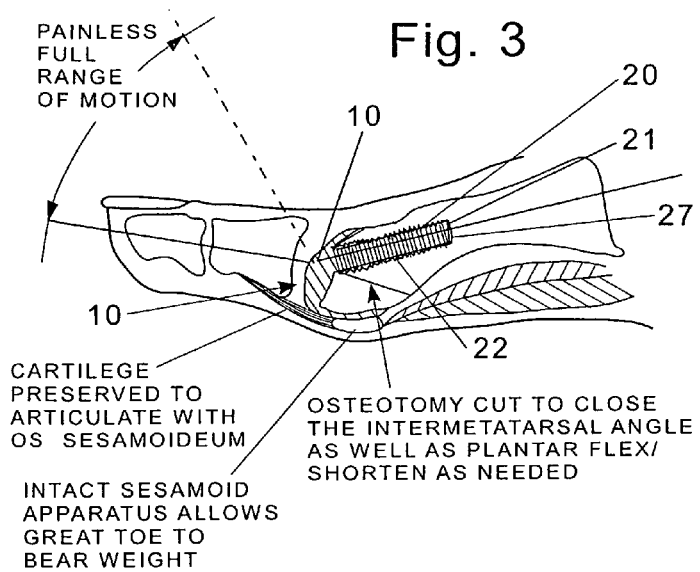
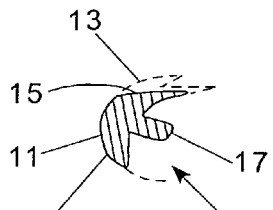
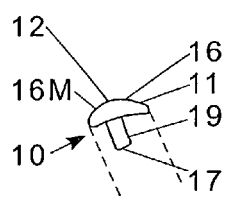
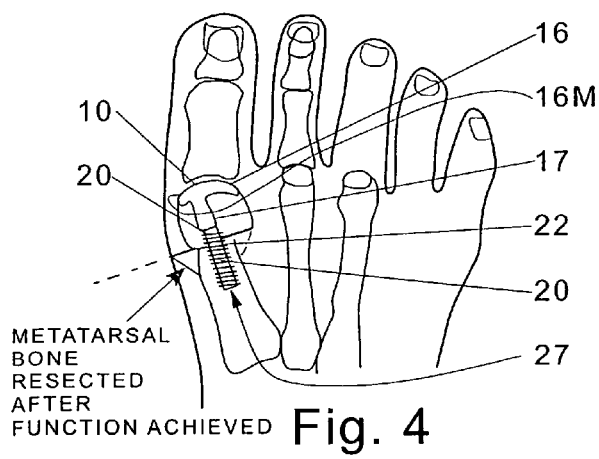
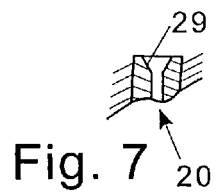
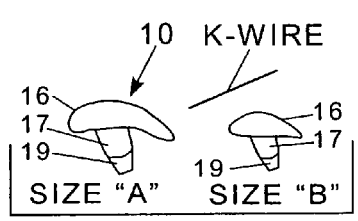
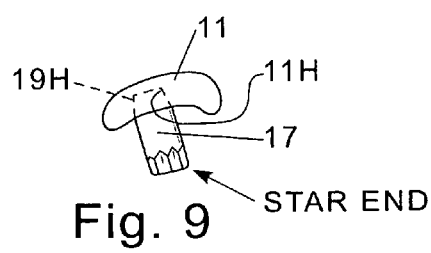

TOE CAP IMPLANT

This claims benefits under 35 USC 119(e) of provisional patent application No. U.S. 60/933,021 filed on Jun. 4, 2007 A.D. The complete specification of that application, including its drawings, of course, is incorporated herein by reference.

FIELD AND PURVIEW OF THE INVENTION

This concerns an implant, which can be embodied, for example, for resolving a jammed great toe joint. The implant can include a metatarsal cap and a cannulated screw, which can be implanted in the metatarsal bone, say, of a human being.

BACKGROUND TO THE INVENTION

A notable problem in the human foot is that of Hallux Rigidus. Such a problem presents a jammed great toe joint, with arthritis principally on the metatarsal side. The great toe has limited, painful, dorsal flexion, and a bunion or dorsal boney spur may be present, which can be painful. Generally, the Hallux Abductus angle is elevated, and the os sesamoideum (sesamoid bone) may rotate to an abnormal lateral position. An elevated intermetatarsal angle generally results.

Currently available great toe hemi-implants, which have a concave articulating surface and are available in stainless steel, are implanted into the phalangeal side of the joint. Such hemi-implants require a removal of the base of the proximal phalanx, and can engender multiple, documented problems for this presentation, among which can include that the amputation of the base of the proximal phalanx to place the hemi-implant results in a loss of the insertion of the intrinsic muscles. The outcome is loss of digital stability often resulting in jamming of the implant onto the metatarsal head, with pain and again decreased motion occurring. Also, as useful as they are in addressing other presentations, the great toe hemi-implant cannot address the elevation in intermetatarsal angle.

The well known Valenti procedure may be attempted to resect the bunion or spur so as to stop jamming. Since the metatarsal head is partially resected to a flat surface in that procedure, normal dorsiflexion motion is lost, and pain can, and often does, return.

It is also known that the metatarsal mal position seen with Hallux Rigidus can be corrected with a thru and thru metatarsal osteotomy fixated with cannulated screws, which are placed over a K-wire guide pin for proper orientation. The K-wire is removed after the screw is placed over it.

It would be desirable to ameliorate if not solve the Hallux Rigidus problem at least in a reasonable number of presentations. It would be desirable to provide alternatives to the art.

A FULL DISCLOSURE OF THE INVENTION

In general, provided is a cap having a head with a convex articular surface and opposite the articular surface an attaching feature that can attach the cap to a bone screw. A combination or ensemble, or a kit with the cap and screw is provided as well.

The invention is useful in arthroplasty.

Significantly, by the invention, the art is advanced in kind. In a particular embodiment, the problem of Hallux Rigidus can be surgically resolved with the invention. Thus, the invention provides for repairing the primary defect of Hallux Rigidus with a metatarsal cap while simultaneously correcting the underlying source of the initial metatarsal misalignment with an osteotomy held with the same screw holding the cap. The invention can be efficient to make and use.

Numerous further advantages attend the invention.

The drawings form part of the specification hereof. With respect to the drawings, which are not necessarily drawn to scale, the following is briefly noted:

FIG. 1 is a side plan view of a problem of Hallux Rigidus.
FIG. 2 is a top plan view of the problem such as in FIG. 1.
FIG. 3 is a side plan view of an embodiment of the invention.
FIG. 4 is a top plan view of the embodiment of FIG. 3.
FIG. 5 is a side view of a toe cap employed in FIGS. 3 and 4.
FIG. 6 is a top view of the toe cap in FIGS. 3-5.
FIG. 7 is a sectional view of an internal taper on a screw.
FIG. 8 shows a K-wire, and a metatarsal cap trial sizer.
FIG. 9 shows a modular head and stem ensemble, assembled.

The invention can be further understood by the detail set forth below, which may be read in view of the drawings. As with the foregoing, such is to be taken in an illustrative and not necessarily limiting sense.

A correction for Hallux Rigidus provided hereby includes an anatomic physiologic metatarsal head cap, which can have a reducing radius dorsally so as to improve dorsal range of motion, and which can fit into a cannulated screw that fixates a metaphyseal metatarsal osteotomy that can do the following: 1) close the inner metatarsal angle; 2) plantar flex the metatarsal head, if necessary; and 3) shorten the metatarsal head, if necessary. A jig, which can be fitted to the distal one third to one half of the metatarsal head, can be employed to remove the abnormal distal cartilage and cut the appropriate osteotomy of the metatarsal. The cannulated screw can be placed over a K-wire that enters distally through a metatarsal cap trial sizer sitting on the prepared metatarsal head surface.

With reference to the drawings, the following is noted:

Cap 10, for example, made of physiologically compatible stainless steel or other suitable material, includes convex head 11 having articular surface 12 that can be defined in relation to a circular circumference 13 by generally circular radial portion 14 and dorsally directable reducing radius 15. More full, offset portion 16 of the head in comparison to less full medial portion 16M of the head can be provided relative to stem 17 that may be have taper 19, for example, being cylindrically tapered, say, with a Morse or Browne & Sharpe taper, or may assume any other suitable shape, for instance, a star shape when viewed from its end. A head 11 and stem 17 may be modular and put together with taper 11M, 17M such as a Morse or Browne & Sharpe taper. Various sized caps with various sized heads and stems can be provided.

Cannulated cancellous bone screw 20, for example, made of physiologically compatible stainless steel or other suitable material, has body 21; threads 22; and interior channel 27 that may be cylindrical throughout and be provided with taper 29, say, a female style, at an end such as with a Morse taper or a Browne & Sharpe taper to receive the stem 16 through the male taper 19 of the cap 10, or be another suitable shape, for instance, a star shape when viewed down its interior channel. The stem 17 and interior channel 27 can provide for pressure or interference fitting of the cap 10 and screw 20. Cannulated screws 20 of any suitable size may be provided, for instance, in sizes ranging from a 5-mm outside diameter (O.D.) to an 8-mm O.D., offered, say, in 0.5-mm increments, for example, a 6.0-mm O.D. cannulated screw. The screw 20 can have any suitable length, for instance, in sizes ranging from a 20-mm to 40-mm length, offered, say, in 2-mm increments, for example, a 38-mm length.

Thus, corrective osteotomy with a beam-central cannulated screw fixation of a medially offset dorsal radius reduced metatarsal cap can be carried out. And so, the complex deformity of Hallux Rigidus can be effectively resolved.

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous adaptations and modifications can be effected within its spirit, the literal claim scope of which is particularly pointed out as follows:

I claim:

1. A toe cap implant comprising an anatomic physiologic metatarsal head cap having a convex articular surface and opposite the articular surface an attaching feature that can attach the head cap to a bone screw, which fixates a metaphyseal metatarsal osteotomy that can do the following:
   A) close an inner metatarsal angle;
   B) plantar flex a metatarsal head, if necessary; and
   C) shorten the metatarsal head, if necessary;
wherein the toe cap implant is useful for a surgical correction for Hallux Rigidus, and which implant includes a more full, offset portion of the head cap in comparison to a less full medial portion of the head cap relative to the attaching feature.

2. The toe cap implant of claim 1, wherein the head cap has a reducing radius dorsally so as to improve dorsal range of motion, and the attaching feature is a stem.

3. The toe cap implant of claim 2, which includes a convex head having an articular surface that can be defined in relation to a circular circumference by a generally circular radial portion and a dorsally directable reducing radius.

4. The toe cap implant of claim 3, in combination with the bone screw, wherein the bone screw is cannulated.

5. The toe cap implant of claim 4, in combination with the cannulated screw, wherein the cannulated screw is a cannulated cancellous bone screw having a body; threads; and an interior channel that is generally cylindrical throughout, which is adapted to receive the attaching feature.

6. The toe cap implant of claim 5, in combination with the cannulated screw, wherein the interior channel is tapered at an end to receive the attaching feature, which is correspondingly tapered.

7. The toe cap implant of claim 2, in combination with the bone screw, wherein the bone screw is cannulated.

8. The toe cap implant of claim 7, in combination with the cannulated screw, wherein the cannulated screw is a cannulated cancellous bone screw having a body; threads; and an interior channel that is generally cylindrical throughout, which is adapted to receive the attaching feature.

9. The toe cap implant of claim 8, in combination with the cannulated screw, wherein the interior channel is tapered at an end to receive the attaching feature, which is correspondingly tapered.

10. The toe cap implant of claim 1, in combination with the bone screw, wherein the bone screw is cannulated.

11. The toe cap implant of claim 10, in combination with the cannulated screw, wherein the cannulated screw is a cannulated cancellous bone screw having a body; threads; and an interior channel that is generally cylindrical throughout, which is adapted to receive the attaching feature.

12. The toe cap implant of claim 11, in combination with the cannulated screw, wherein the interior channel is tapered at an end to receive the attaching feature, which is correspondingly tapered.

* * * * *